United States Patent [19]
Tsuji et al.

[11] Patent Number: 4,491,547
[45] Date of Patent: Jan. 1, 1985

[54] FLUOROMETHYLTHIOACETIC ACID COMPOUNDS

[75] Inventors: Teruji Tsuji, Osaka; Hisao Sato, Nara; Yoshio Hamashima, Kyoto, all of Japan

[73] Assignee: Shionogi & Co., Ltd., Osaka, Japan

[21] Appl. No.: 333,678

[22] Filed: Dec. 23, 1981

[30] Foreign Application Priority Data

Dec. 26, 1980 [JP] Japan .................................. 55-185781

[51] Int. Cl.$^3$ ................. C07C 153/017; C07C 153/00
[52] U.S. Cl. ................................. 260/455 R; 564/192; 562/602; 562/605; 560/153
[58] Field of Search ................. 564/192; 562/602, 605; 260/455 R; 560/153

[56] References Cited

U.S. PATENT DOCUMENTS 3,297,692  1/1967  Flynn et al. ........................... 544/29

Primary Examiner—Henry R. Jiles
Assistant Examiner—Robert C. Whittenbaugh
Attorney, Agent, or Firm—Wenderoth, Lind & Ponack

[57] ABSTRACT

Monofluoromethylthioacetic acid ($FCH_2SCH_2COOH$) or difluoromethylthioacetic acid ($F_2CHSCH_2COOH$), or its derivative at the carboxy group can be prepared e.g. by treating a thioglycolic acid ester with monolfuorohalomethane or difluorohalomethane in the presence of a base if required followed by a conventional modification of the produced ester e.g. to make an acid by hydrolysis, a salt by neutralization, a halide with a halogenating agent, and from acid halide or anhydride an ester with an alcohol, or an amide with an amine. These compounds are useful intermediates in the production of medicinal and agricultural chemicals.

4 Claims, No Drawings

FLUOROMETHYLTHIOACETIC ACID COMPOUNDS

SUMMARY OF INVENTION

This invention relates to novel fluoromethylthioacetic acid compounds useful as indispensable intermediates for the production of useful substances e.g. organic solvents or medical or agricultural chemicals, including antibacterial penicillins and cephalosporins. By chemical nomenclature the compounds of this invention can be defined as monofluoromethylthioacetic acid or difluoromethylthioacetic acid, or the derivatives at the carboxy group.

The compounds can be prepared e.g. by the action of monofluoromethyl halide or difluoromethyl halide with thioglycolate ester in the presence of a base.

The penicillins or cephalosporins having an acyl moiety derived from these carboxylic acids are found to show excellent antibacterial activity as compared with prior art compounds.

PRIOR ART

Trifluoromethylthioacetic acid has been known as the acyl source for the side chain of a synthetic cephalosporin as disclosed in British Pat. No. 1,393,348, but the final product has never been marketed so far. This acid has been synthesized by condensing a trifluoromethyl mercaptide salt with iodoacetic acid at room temperature for several days.

An alkylthioacetic acid has been known to be the acyl source for the side chain of some synthetic cephalosporins as disclosed in U.S. Pat. No. 3,297,692. The acid is prepared by the action of an alkanethiol with haloacetic acid, preferably in ester form.

COMPOUNDS

The novel compounds of this invention are represented by the formula:

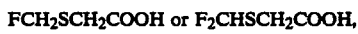

FCH$_2$SCH$_2$COOH or F$_2$CHSCH$_2$COOH, or carboxy derivatives thereof.

Representative carboxy derivatives are salts, esters, amides, halides, anhydrides and the like.

Preferable carboxy derivatives are light metal salts e.g. alkali metal salts or alkaline earth metal salts; alkyl esters e.g. C$_1$ to C$_8$-, more preferably C$_1$ to C$_4$-, optionally branched, cyclic or unsaturated alkyl, optionally substituted; aralkyl ester, e.g. monocyclic or dicyclic aralkyl ester optionally substituted; aryl ester e.g. mono- or di-cyclic aryl ester, optionally substituted; thiol ester e.g. C$_1$ to C$_4$-alkylthiol ester or monocyclic arylthiol ester, optionally substituted; amide e.g. C$_1$ to C$_9$-alkyl amide or monocyclic or dicyclic arylamide, optionally substituted, including hydrazide, semicarbazide and thiosemicarbazide; halide e.g. chloride or bromide; or anhydride e.g. symmetrical or mixed anhydride with C$_1$ to C$_6$ alkanoic acid or C$_2$ to C$_6$ alkoxyformic acid. The optional substituent can be halogen, C$_1$ to C$_4$-alkoxy, oxo, nitro, C$_1$ to C$_4$-alkyl, C$_1$ to C$_4$ alkanoyl or C$_2$ to C$_6$-carbalkoxy. The aryl group can be a five or six membered heterocyclic group having up to four hetero atoms selected from oxygen, nitrogen and sulfur.

Among these, light metal salts, alkyl esters, aralkyl esters, anhydrides and halides are important.

PROCESSES

The compounds of this invention are prepared, for example, by treating the corresponding thioglycolic acid or its derivative at the carboxy group with monofluoromethyl halide or difluoromethyl halide in the presence of a base.

The ester can preferably be a C$_1$ to C$_8$-alkyl ester, monocyclic aralkyl ester, dicyclic aralkyl ester, aryl ester or alkylamide. More preferable esters are C$_1$ to C$_6$ alkyl esters and monocyclic or dicyclic aralkyl esters.

The base can preferably be e.g. an alkali metal, alkali metal hydride, alkali metal hydroxide, alkali metal alkoxide, alkali metal phenoxide, C$_3$ to C$_{12}$-tertiary amine or quaternary ammonium hydroxides or the like.

Gaseous monofluoromethyl halide or difluoromethyl halide can be fed into the reaction mixture either by observing the weight of the mixture or by controlling the rate of the gas stream. Of course, the reagent may be dissolved in a solvent for more accurate estimation of the amount to be added. Usually, the thioglycolic acid compound is treated with 1 to 5, preferably 1 to 2 equivalents of the halide reagent.

The reaction is an exothermic reaction which can proceed under cooling or with mild heating. The reaction proceeds smoothly if the mercapto group of thioglycolic acid or its derivative is converted into an intermediary mercaptide group. The presence of a base is necessary for this purpose.

The reaction is preferably carried out at −20° C. to 100° C., more preferably at 0° C. to 70° C. Then the reaction usually takes about 0.5 to 30 hours, generally 1 to 5 hours.

The reaction is preferably carried out in an inert solvent to dissolve the starting salt and reagent e.g. an industrially available solvent such as an alcohol, ether, amide, sulfoxide, nitrohydrocarbon, nitrle or the like, or mixtures thereof. Non-polar solvent e.g. industrially available hydrocarbon or halohydrocarbon solvent may be used at the same time to dissolve the starting material if required.

After the reaction, the solvent, unreacted starting materials, reagent and by-products are removed from the reaction mixture by a conventional manner e.g. neutralization, concentration, extraction, distillation, washing, etc., and the resulted crude product can further be purified conventionally e.g. by drying, distillation, chromatography, crystallization at low temperature etc.

Preferable starting materials are alkyl esters and aralkyl esters. The derivatives which are unstable under the reaction condition e.g. acid halides or anhydrides can hardly be used.

Under a preferable condition, thioglycolate is dissolved in an alcohol, amide or ether solvent (3 to 8 parts w/w), alkali metal, alkali metal hydride or alkali metal alkoxide (1 to 1.5 equivalents) is added to form a mercaptide and then monofluorochloromethane or difluorochloromethane is added by passing the gaseous reagent or mixing a solution of the reagent in a solvent at 10° C. to 40° C. for 1 to 10 hours.

Thus produced fluoromethylthioacetic acids and their derivatives can further be converted to other types of derivatives by utilizing a conventional method in the art. Thus, for example, the alkyl ester can be hydrolyzed with an aqueous base e.g. aqueous alkali at around room temperature or with heating to afford a carboxylate salt; the carboxylate salt can be neutralized with a strong acid e.g. mineral acid or sulfonic acid to give the corresponding carboxylic acid. The carboxylic acid gives a salt with a base. The halogenating reagent e.g. thionyl halide, oxalyl halide, phosphorus oxyhalide or phosphorus halide in the presence of an acid scavenger e.g. pyridine, picoline, triethylamine, etc., preferably under cooling, makes an acid halide from the carboxylic acid. An alcohol or amine with said acid halide makes an ester or amide. Anhydrides of the carboxylic acid with an alkanoic acid, sulfonic acid or mineral acid can also be produced by a conventional manner. Alkali metal or alkaline earth metal salts can be prepared conventionally by neutralizing the free acid or by cation exchange.

HOW TO USE THE COMPOUNDS OF THIS INVENTION

The compounds of this invention are useful as intermediates for synthesizing useful products e.g. medical or agricultural chemicals, or as solvents. For example, the acids and esters can be used as solvents for organic reactions, as they can stably dissolve various materials. Further the acid halide prepared through e.g. ester, carboxylic salt and free carboxylic acid can react with 6-aminopenicillanic acid or 7-aminocephalosporanic acid or its 3-heterothio-methyl derivative or 1-oxadethia analog with a base e.g. triethylamine or picoline to give a potent antibacterial compound, i.e. the corresponding penicillin or cephalosporin compound according to a manner conventional in the art.

Such penicillins and cephalosporins can be injected into a patient suffering from a bacterial infection caused by a sensitive strain of bacteria at a daily dose of 1 to 2 grams in three times. Furthermore, the acyl part of the compounds can also play a role of modifying the structure of various medicinal, veterinary or other useful substances.

EXAMPLES

Following examples illustrate the embodiments of this invention. Amounts in equivalents show molar equivalents. For drying solutions, use is made of magnesium sulfate, and vacuum evaporation is used generally for concentrating purposes.

EXAMPLE 1

(Difluoromethylthioacetic acid ester)

(a) R=CH$_3$

To a solution of sodium (1.1 equivalent) in methanol (3.2 parts by weight) is added methyl thioglycolate, and the mixture is stirred at 5° C. to 30° C. for 10 to 30 minutes to produce the corresponding sodium mercaptide. To this solution is introduced 2 mole equivalents of difluorochloromethane. After 4 hours at 30° C., the mixture is neutralized with hydrochloric acid and concentrated in vacuum to obtain crude methyl difluoromethylthioacetate. This can further be purified by distillation. Yield: 51%. bp$_{29}$ 78° C.

NMR: $\delta_{ppm}^{CDCl_3}$ 7.05t ($J_{HF}$=56 Hz).

(b) R=C$_2$H$_5$

A solution of sodium (1.1 equivalent) in ethanol (5.2 parts by weight) is mixed with ethyl thioglycolate, and the mixture is stirred at 5° C. to 30° C. for 10 to 30 minutes to produce the corresponding sodium mercaptide. To this solution is introduced about 2 mole equivalents of gaseous difluorochloromethane. After 3 hours at 25° to 50° C., the mixture is neutralized with hydrochloric acid and concentrated in vacuum to obtain crude ethyl difluoromethylthioacetate. This can further be redistilled to give a pure sample. Yield: 66%. bp$_{35}$ 88°–91° C.

NMR: $\delta_{ppm}^{CDCl_3}$ 7.05 t ($J_{HF}$=56 Hz).

The same ester can be prepared by using 1.2 mole equivalents of sodium ethoxide in 5.0 parts by weight of N,N-dimethylformamide at 13° C. for 5 hours, followed by reaction at room temperature overnight to give the same product after distillation. Yield: 57%. bp$_3$ 47°–49° C.

The same ester can also be made by using 1.2 mole equivalents of sodium ethoxide in 6.3 parts by weight of dimethoxyethane for 4 hours at 10° C. to afford ethyl difluoromethylthioacetate. Yield 67%. bp$_3$ 42°–47° C.

EXAMPLE 2

(Monofluoromethylthioacetic acid ester)

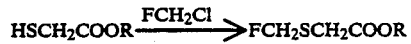

(a) R=C$_2$H$_5$

To a solution of sodium ethoxide (1 mole equivalent) in N,N-dimethylformamide (4.9 parts by weight) is added ethyl thioglycolate, and the mixture is stirred at 5° C. to 30° C. for 10 to 30 minutes to produce the corresponding sodium mercaptide. To this solution is introduced 2 mole equivalents of fluorochloromethane. After standing for 1 hour at 20° to 37° C., the reaction mixture is neutralized with hydrochloric acid and concentrated in vacuum. Obtained crude ethyl fluoromethylthioacetate is purified by distillation. Yield: 49%. bp$_{19}$ 86° C.

NMR: $\delta_{ppm}^{CDCl_3}$ 5.58d (J=$_{HF}$52 Hz).

(b) R=—CH(C$_6$H$_5$)$_2$

To a solution of sodium hydride (1 mole equivalent) in dimethylformamide (4.7 parts by weight) is added diphenylmethyl thioglycolate, and the mixture is stirred at 5° C. to 30° C. for 10 to 30 minutes to give the corresponding sodium mercaptide. To this solution is introduced 2 mole equivalents of fluorochloromethane. After 1 hour at 20° C., the mixture is neutralized with hydrochloric acid and concentrated in vacuum to obtain crude diphenylmethyl monofluoromethylthioacetate. Yield: 87%.

NMR: $\delta_{ppm}^{CDCl_3}$ 5.48d (J$_{HF}$=51 Hz).

EXAMPLE 3

(Free acid)

A solution of ethyl difluoromethylthioacetate in aqueous 25% potassium hydroxide (1.12 equivalents) is stirred for 2 to 3 hours at room temperature. The reaction mixture containing the corresponding potassium salt as aqueous solution is covered by ether, adjusted with concentrated hydrochloric acid to pH 1 to 2, and saturated with sodium chloride. The separated ether layer is washed with saline, dried over magnesium sulfate and concentrated. The product is kept under reduced pressure to purge volatile materials giving difluoromethylthioacetic acid. Yield: 97%.

NMR: $\delta_{ppm}^{CDCl_3}$ 6.95t ($J_{HF}=56$ Hz)1H, 3.6s2H, 10.55s1H.

EXAMPLE 4

(Acid halide)

To a solution of difluoromethylthioacetic acid in ether (15 parts by weight) is added phosphorus pentachloride (1 equivalent) under ice cooling, and the mixture is stirred at 5° to 15° C. for 2 hours. The mixture is then concentrated to dryness, dissolved in carbon tetrachloride (9 parts by weight) and concentrated in vacuum to remove phosphorus oxychloride. The remaining liquid is distilled under reduced pressure to give difluoromethylthioacetyl chloride. Yield: 93.2%. bp$_{13}$ 42°-50° C. Colorless oil.

IR: $\nu_{max}^{film}$ 1800 cm.$^{-1}$

EXAMPLE 5

(Ester)

(a) R=t—C$_4$H$_9$

To a stirred and ice cooled solution of t-butanol (1.2 equivalents) and pyridine (1.3 equivalents) in dichloromethane (5 parts by weight) is dropwise added difluoromethylthioacetyl chloride, and the mixture is stirred for 4 hours. The mixture is washed with water, dried and concentrated in vacuum. The residual liquid is distilled to give t-butyl difluoromethylthioacetate as an oil. Yield: 48.6%.

NMR: $\delta_{ppm}^{CDCl_3}$ 6.93 t ($J_{HF}=54$ HZ).
IR: $\nu_{max}^{film}$ 1730 cm.$^{-1}$ (b) R=p-methoxybenzyl To a stirred and ice cooled solution of p-methoxybenzyl alcohol (1.2 equivalents) in dichloromethane (5 parts by weight) is added dropwise difluoromethylthioacetyl chloride, and the mixture is stirred for 4 hours. The mixture is washed with water, dried and concentrated. The residual liquid is distilled to give oily p-methoxybenzyl difluoromethylthioacetate. Yield: 80.4%.

NMR: $\delta_{ppm}^{CDCl_3}$ 6.85t ($J_{HF}=56$ Hz).
IR: $\nu_{max}^{film}$ 1738 cm$^{-1}$.

(c) R=C$_2$H$_5$OC$_2$H$_4$—

To a stirred and ice cooled solution of 2-ethoxyethanol (1.2 equivalents) and pyridine (1.3 equivalents) in dichloromethane (5 parts by weight) is dropwise added difluoromethylthioacetyl chloride. After stirring for 4 hours, the mixture is washed with saline, dried and concentrated. The residual liquid is distilled to give oily 2-ethoxyethyl difluoromethylthioacetate. Yield: 60%.

NMR: $\delta_{ppm}^{CDCl_3}$ 7.0t ($J_{HF}=56$ Hz).
IR: $\nu_{max}^{film}$ 1738 cm$^{-1}$.

EXAMPLE 6

(Thiol ester)

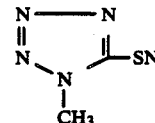
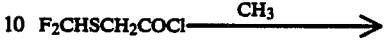
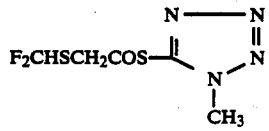

To a stirred and ice cooled solution of sodium 1-methyl-5-tetrazolylmercaptide in water (10 parts by weight) is added dropwise difluoromethylthioacetyl chloride (0.83 equivalent). After 3 hours, the mixture is extracted with dichloromethane. The extract solution is washed with saline, dried and concentrated. The residue is chromatographed over silica gel to give 5-difluoromethylthioacetylthio-1-methyltetrazole. Yield: 70%.

NMR: $\delta_{ppm}^{CDCl_3}$ 6.95 t ($J_{HF}=55$ Hz).
IR: $\nu_{max}^{film}$ 1718, 1750 cm$^{-1}$.

EXAMPLE 7

(Amide)

(a) amine=morpholine

To a solution of morpholine (2.5 equivalents) in dichloromethane (5 parts by weight) is dropwise added difluoromethylthioacetyl chloride with ice cooling, and the mixture is kept standing for 3 hours, washed with saline, dried and concentrated in vacuum. The residual oil is 4-(difluoromethylthioacetyl)morpholine. Yield: 39.5%.

NMR: $\delta_{max}^{CDCl_3}$ 6.93 t ($J_{HF}=56$ Hz).
IR: $\nu_{max}^{film}$ 1640 cm$^{-1}$.

(b) amine=aniline

To a stirred solution of aniline (2.5 equivalents) in dichloromethane (5 parts by weight) is dropwise added difluoromethylthioacetyl chloride with ice cooing, and the mixture is kept standing for 3 hours. The mixture is washed with water, dried and concentrated. The residual oil is difluoromethylthioacetoanilide. Yield: 88.8%. mp. 58°-61° C.

NMR: $\delta_{ppm}^{CDCl_3}$ 6.88 t ($J_{HF}=56$ Hz).
IR: $\nu_{max}^{CHCl_3}$ 1688 cm$^{-1}$.

(c) amine=6-APA

To a stirred and ice cooled solution of 6-aminopenicillanic acid (1.1 equivalents) in aqueous sodium hydrogen carbonate (3.5 equivalents) solution is added dropwise a solution of difluoromethylthioacetyl chloride in ether (5 parts by weight), and the mixture is stirred for 40 minutes. The reaction mixture is washed with ethyl acetate, acidified with hydrochloric acid to pH 2, and extracted with ethyl acetate. The extract solution is washed with saline, dried and concentrated to give 6-(difluoromethylthioacetamido)penicillanic acid. Yield: 66%.

NMR: $\delta_{ppm}^{CD3COCD3}$ 7.03 t ($J_{HF}$=57 Hz), 5.32 q (J=7.2;4 Hz), 5.27 d (J=4 Hz)2H, 4.37 s 1H, 3.68 s 2H, 1.58 s3H, 1.65 s3H.

EXAMPLE 8

(Anhydride)

R=Isobutyl

To a stirred solution of triethylamine (1.4 equivalents) and isovaleric acid (1.3 equivalents) in tetrahydrofuran (5 parts by weight) is dropwise added difluoromethylthioacetyl chloride at −30° C., and the mixture is left standing for 1 hour. After-removing separated crystals by filtration, the reaction mixture is concentrated in vacuum to leave difluoromethylthioacetic isovaleric anhydride.
Yield: 83.6%.
NMR: $\delta_{ppm}^{CDCl3}$ 6.92 t ($J_{HF}$=56 Hz).
IR: $\nu_{max}^{film}$ 1820, 1750 cm$^{-1}$.
What we claim is:

1. A compound selected from the group consisting of monofluoromethylthioacetic acid, difluoromethylthioacetic acid, and a derivative at the carboxy group thereof selected from the group consisting of a light metal salt; an optionally branched, optionally cyclic, optionally unsaturated or optionally substituted $C_1$ to $C_8$ alkyl ester; an optionally substituted benzyl or diphenylmethyl ester; an optionally substituted alkylthiolester; an optionally substituted $C_1$ to $C_9$ alkylamide or anilide; an acid anhydride with a $C_1$ to $C_6$ alkanoic acid or a $C_2$ to $C_6$ alkoxyformic acid; and a halide,
 in which the substituent is selected from the group consisting of halogen, $C_1$ to $C_4$ alkoxy, oxo, nitro, $C_1$ to $C_4$ alkyl, $C_1$ to $C_4$ alkanoyl and $C_2$ to $C_6$ carbalkoxy.

2. A compound according to claim 1 that is a $C_1$ to $C_4$ optionally branched alkyl ester, optionally substituted by $C_1$ to $C_4$ alkoxy.

3. A compound according to claim 1 that is a benzyl or diphenylmethyl ester.

4. a compound according to claim 1 that is a chloride, bromide or acid anhydride.

* * * * *